(12) United States Patent
Basadonna et al.

(10) Patent No.: US 11,812,985 B2
(45) Date of Patent: Nov. 14, 2023

(54) ENDOSCOPY SYSTEMS AND METHODS OF USE THEREOF

(71) Applicant: Enlightenvue, Inc., Denver, CO (US)

(72) Inventors: Giacomo Basadonna, Haddam, CT (US); Alan Lucas, Brookline, MA (US)

(73) Assignee: EnlightenVue, INC., Denver, CO (US)

( * ) Notice: Subject to any disclaimer, the term of this patent is extended or adjusted under 35 U.S.C. 154(b) by 623 days.

(21) Appl. No.: 16/627,676

(22) PCT Filed: Jun. 28, 2018

(86) PCT No.: PCT/US2018/039934
§ 371 (c)(1),
(2) Date: Dec. 30, 2019

(87) PCT Pub. No.: WO2019/006081
PCT Pub. Date: Jan. 3, 2019

(65) Prior Publication Data
US 2020/0155190 A1 May 21, 2020

Related U.S. Application Data

(60) Provisional application No. 62/527,625, filed on Jun. 30, 2017.

(51) Int. Cl.
*A61B 1/00* (2006.01)
*A61B 17/32* (2006.01)
(Continued)

(52) U.S. Cl.
CPC .. *A61B 17/320036* (2013.01); *A61B 1/00078* (2013.01); *A61B 1/00087* (2013.01);
(Continued)

(58) Field of Classification Search
CPC . A61B 1/00078; A61B 1/00087; A61B 1/317; A61B 2017/00402; A61B 17/320036
See application file for complete search history.

(56) References Cited

U.S. PATENT DOCUMENTS 4,470,407 A 9/1984 Hussein
4,576,145 A 3/1986 Tsuno et al.
(Continued)

FOREIGN PATENT DOCUMENTS

CN 1719997 A 1/2006
CN 102137615 A 7/2011
(Continued)

OTHER PUBLICATIONS

Office Action dated Jun. 13, 2022; in Japanese Application No. 2019-572450 filed Dec. 19, 2022; in 9 pages.
(Continued)

*Primary Examiner* — Timothy J Neal
(74) *Attorney, Agent, or Firm* — Knobbe, Martens, Olson & Bear, LLP

(57) ABSTRACT

In some embodiments, endoscopy systems and/or methods of using endoscopy systems are described. In some embodiments, an endoscopy system comprises one or more of piezoelectric elements or hooked blades. In some embodiments, stylets for use with an endoscopy system are described. In some embodiments, the endoscopy systems are useful for orthopedic procedures. In some embodiments, the endoscopy systems are useful for arthroscopic procedures.

16 Claims, 8 Drawing Sheets

(51) Int. Cl.
  *A61B 1/018* (2006.01)
  *A61B 1/07* (2006.01)
  *A61B 1/317* (2006.01)
  *A61B 17/00* (2006.01)

(52) U.S. Cl.
  CPC ............... *A61B 1/018* (2013.01); *A61B 1/07* (2013.01); *A61B 1/317* (2013.01); *A61B 2017/00402* (2013.01)

(56) References Cited

U.S. PATENT DOCUMENTS

| | | | |
|---|---|---|---|
| 4,961,738 | A | 10/1990 | Mackin |
| 5,025,778 | A | 6/1991 | Silverstein et al. |
| 5,090,959 | A | 2/1992 | Samson et al. |
| 5,116,317 | A | 5/1992 | Carson et al. |
| 5,152,277 | A | 10/1992 | Honda et al. |
| 5,263,928 | A | 11/1993 | Trauthen et al. |
| 5,263,931 | A | 11/1993 | Miller |
| 5,308,323 | A | 5/1994 | Sogawa et al. |
| 5,323,765 | A | 6/1994 | Brown |
| 5,464,394 | A | 11/1995 | Miller et al. |
| 5,765,568 | A | 6/1998 | Sweezer et al. |
| 5,810,776 | A | 9/1998 | Bacich et al. |
| 6,110,104 | A | 8/2000 | Suzuki et al. |
| 6,585,639 | B1 | 7/2003 | Kotmel et al. |
| 6,958,035 | B2 | 10/2005 | Friedman et al. |
| 7,837,699 | B2 * | 11/2010 | Yamada ......... A61B 17/320092 600/459 |
| 8,038,598 | B2 | 10/2011 | Khachi |
| 8,333,691 | B2 | 12/2012 | Schaaf |
| 8,784,298 | B2 | 7/2014 | Fructus et al. |
| 9,370,295 | B2 | 6/2016 | Kienzle et al. |
| 10,244,928 | B2 | 4/2019 | Konwitz et al. |
| 10,285,571 | B2 | 5/2019 | Rozenfeld et al. |
| 10,582,834 | B2 | 3/2020 | Hastings |
| 10,582,835 | B2 | 3/2020 | Surti et al. |
| 10,588,497 | B2 | 3/2020 | Konwitz et al. |
| 10,687,698 | B2 | 6/2020 | Basadonna et al. |
| 11,051,685 | B2 | 7/2021 | Basadonna et al. |
| 11,141,045 | B2 | 10/2021 | Kucharski et al. |
| 2002/0028986 | A1 | 3/2002 | Thompson |
| 2002/0128536 | A1 | 9/2002 | Zigler |
| 2003/0065318 | A1 | 4/2003 | Pendekanti |
| 2003/0088210 | A1 | 5/2003 | Miskolczi et al. |
| 2003/0181785 | A1 | 9/2003 | Viebach et al. |
| 2004/0003819 | A1 | 1/2004 | St. Goar et al. |
| 2004/0097788 | A1 | 5/2004 | Mourlas et al. |
| 2004/0225191 | A1 | 11/2004 | Sekine et al. |
| 2005/0049525 | A1 | 3/2005 | Yamada et al. |
| 2005/0075711 | A1 | 4/2005 | Neary |
| 2005/0272975 | A1 | 12/2005 | McWeeney et al. |
| 2006/0064059 | A1 | 3/2006 | Gelfand et al. |
| 2006/0184048 | A1 | 8/2006 | Saadat |
| 2006/0235458 | A1 | 10/2006 | Belson |
| 2007/0129605 | A1 | 6/2007 | Schaaf |
| 2007/0287886 | A1 | 12/2007 | Saadat |
| 2008/0058591 | A1 | 3/2008 | Saadat et al. |
| 2008/0058836 | A1 | 3/2008 | Moll et al. |
| 2008/0091062 | A1 | 4/2008 | Terliuc |
| 2008/0194999 | A1 | 8/2008 | Yamaha et al. |
| 2008/0294037 | A1 | 11/2008 | Richter |
| 2009/0076331 | A1 | 3/2009 | Konwitz et al. |
| 2009/0082623 | A1 | 3/2009 | Rothe et al. |
| 2010/0063358 | A1 | 3/2010 | Kessler |
| 2010/0081873 | A1 | 4/2010 | Tanimura et al. |
| 2011/0054326 | A1 | 3/2011 | Barnett |
| 2011/0092766 | A1 | 4/2011 | Monassevitch et al. |
| 2011/0184233 | A1 | 7/2011 | Fructus et al. |
| 2012/0095292 | A1 | 4/2012 | Gunday et al. |
| 2012/0238815 | A1 | 9/2012 | Komi et al. |
| 2013/0023920 | A1 | 1/2013 | Terliuc et al. |
| 2013/0053644 | A1 | 2/2013 | Smith et al. |
| 2014/0024897 | A1 | 1/2014 | Inoue et al. |
| 2014/0039253 | A1 | 2/2014 | Fang et al. |
| 2014/0088362 | A1 | 3/2014 | Terliuc et al. |
| 2014/0249569 | A1 | 9/2014 | Kusleika |
| 2014/0378771 | A1 | 12/2014 | St. Onge et al. |
| 2015/0065794 | A1 | 3/2015 | Knight et al. |
| 2015/0150442 | A1 | 6/2015 | Tafti et al. |
| 2015/0314110 | A1 | 11/2015 | Park |
| 2015/0351611 | A1 | 12/2015 | Hlozek |
| 2015/0352337 | A1 | 12/2015 | Iga et al. |
| 2016/0095500 | A1 | 4/2016 | Kumagai et al. |
| 2016/0095508 | A1 | 4/2016 | Terliuc et al. |
| 2016/0144155 | A1 | 5/2016 | Simpson et al. |
| 2016/0367120 | A1 | 12/2016 | Dupont et al. |
| 2017/0027433 | A1 | 2/2017 | Terliuc |
| 2017/0027458 | A1 | 2/2017 | Glover et al. |
| 2017/0035277 | A1 | 2/2017 | Kucharski et al. |
| 2017/0354318 | A1 | 12/2017 | Rogers et al. |
| 2018/0084971 | A1 | 3/2018 | Truckai et al. |
| 2018/0160893 | A1 | 6/2018 | Truckai et al. |
| 2018/0184892 | A1 | 7/2018 | Truckai et al. |
| 2018/0326144 | A1 | 11/2018 | Truckai et al. |
| 2018/0333043 | A1 | 11/2018 | Terliuc et al. |
| 2018/0338673 | A1 | 11/2018 | Krimsky et al. |
| 2019/0104932 | A1 | 4/2019 | Truckai et al. |
| 2019/0191983 | A1 | 6/2019 | Terliuc |
| 2019/0254649 | A1 | 8/2019 | Walters et al. |
| 2019/0282078 | A1 | 9/2019 | Terliuc et al. |
| 2019/0343372 | A1 | 11/2019 | Cornhill et al. |
| 2019/0380715 | A1 | 12/2019 | Goldin et al. |
| 2020/0164186 | A1 | 5/2020 | Terliuc et al. |
| 2020/0237200 | A1 | 7/2020 | Moktali et al. |
| 2020/0281450 | A1 | 9/2020 | Terliuc et al. |
| 2022/0175233 | A1 | 6/2022 | Basadonna et al. |
| 2022/0211249 | A1 | 7/2022 | Kucharski et al. |

FOREIGN PATENT DOCUMENTS

| | | |
|---|---|---|
| CN | 111065329 A | 4/2020 |
| EP | 3644851 | 5/2020 |
| JP | H01104238 A | 4/1989 |
| JP | H02021292 A | 1/1990 |
| JP | H03-139345 A | 6/1991 |
| JP | H06181879 A | 7/1994 |
| JP | H10 267634 A | 10/1998 |
| JP | 2005-73746 A | 3/2005 |
| JP | 4074169 B2 | 4/2008 |
| JP | 2008538709 A | 11/2008 |
| JP | 2011067399 A | 4/2011 |
| JP | 2012504019 A | 2/2012 |
| JP | 2011529724 | 7/2012 |
| JP | 2014-226338 A | 12/2014 |
| JP | 2016182302 A | 10/2016 |
| JP | 2018-525197 A | 9/2018 |
| JP | 2020-526278 | 8/2020 |
| KR | 2020-37777 | 4/2020 |
| WO | WO 1995/018562 A1 | 7/1995 |
| WO | WO 2006/113544 A2 | 10/2006 |
| WO | WO 2013/064060 A1 | 5/2013 |
| WO | WO 2019/006081 | 1/2019 |

OTHER PUBLICATIONS

Amendment (dated Sep. 2022), Decision to Grant (dated Nov. 7, 2022) in Japanese Application No. 2019-572450 filed Dec. 19, 2022; in 17 pages.
Extended European Search Report for EP Application No. 18825309 dated May 11, 2021.
International Preliminary Report on Patentability for PCT Application No. PCT/US18/39934 dated Dec. 31, 2019.
International Search Report and Written Opinion for PCT Application No. PCT/US18/39934 dated Sep. 19, 2018.
Partial Supplementary European Search Report for EP Application No. 18825309 dated Jan. 20, 2021.
Patel, et al., Interventional radiology-operated endoscopy using the LithoVue disposable endoscope: Approach, technical success, clini-

(56) References Cited

OTHER PUBLICATIONS cal outcomes, and complications; Indian Journal of Radiology and Imaging, Jul.-Sep. 2018;28(3): 350-353.

* cited by examiner

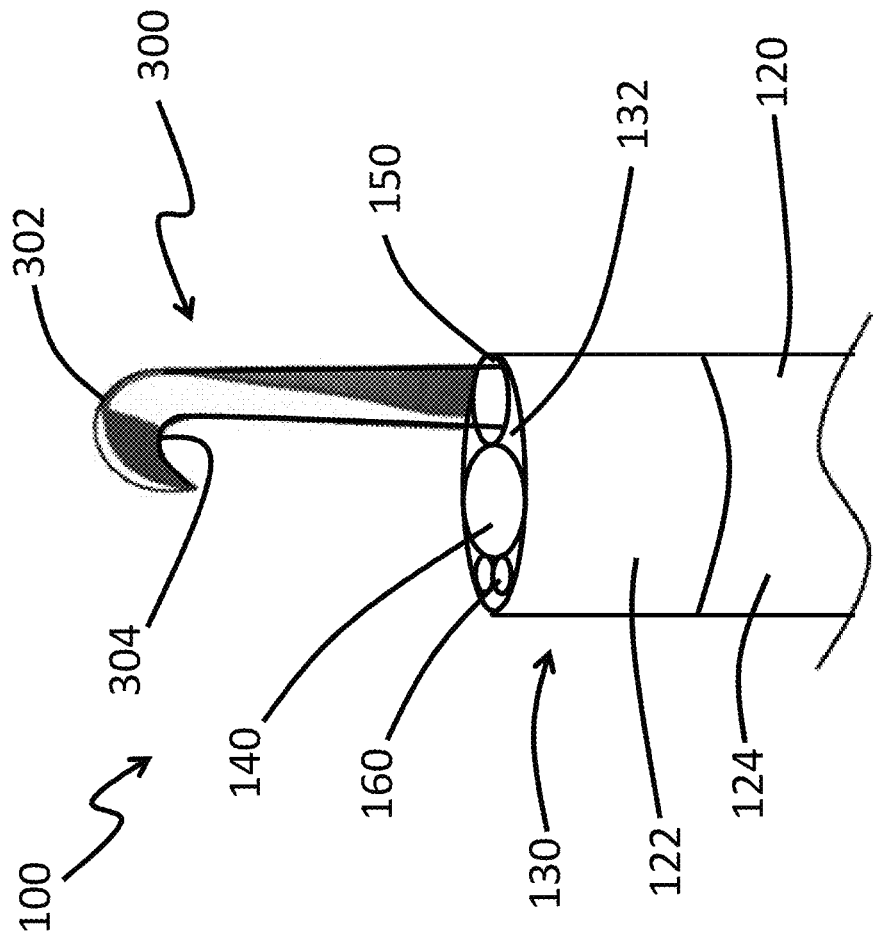

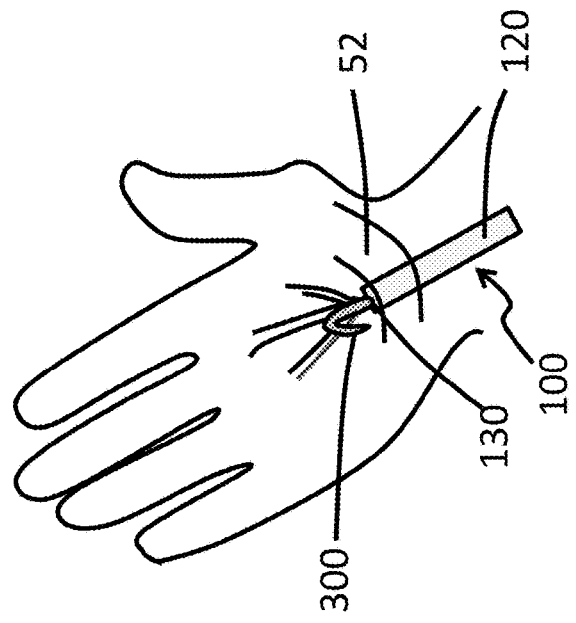
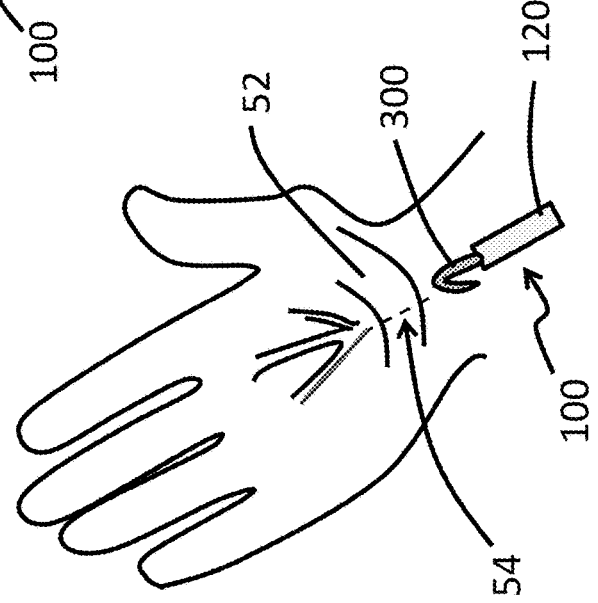
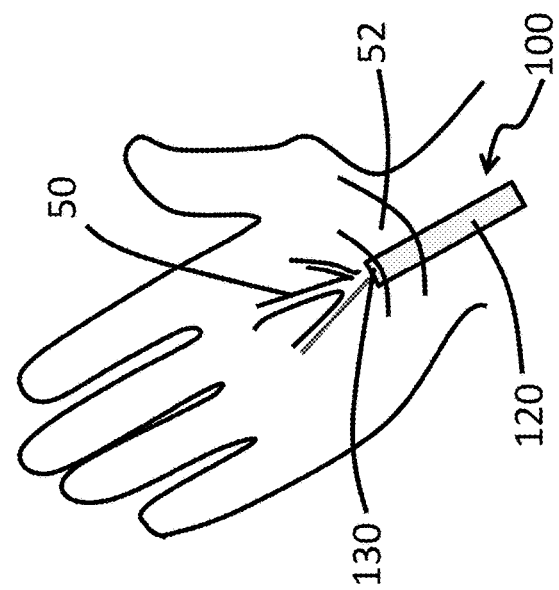

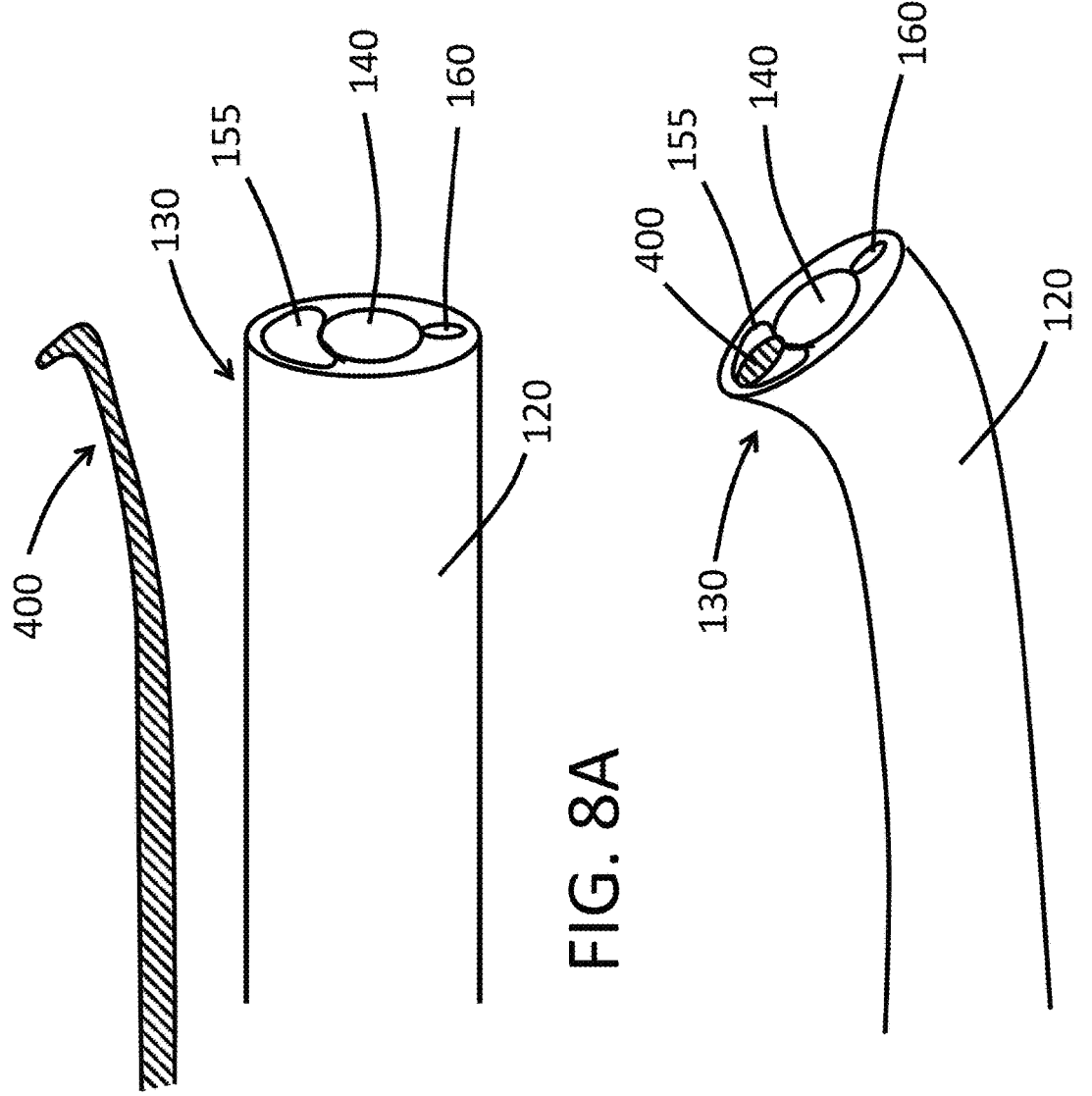

ENDOSCOPY SYSTEMS AND METHODS OF USE THEREOF

INCORPORATION BY REFERENCE

This application claims the benefit of International Application No. PCT/US2018/039934 filed Jun. 28, 2018, which claims the benefit of U.S. Provisional Application No. 62/527,625 filed Jun. 30, 2017, which is hereby incorporated by reference in its entirety. This application incorporates by reference the entirety of International Application No. PCT/US2016/045417 designating the United States, filed on Aug. 3, 2016. The International Application was published in English as WO 2017/027299 A1 on Feb. 16, 2017. The priority US Application of the International Application, U.S. application Ser. No. 14/821,579 filed Aug. 7, 2015, published as US Pub. No. 2017/0035277 on Feb. 9, 2017, is also incorporated by reference in its entirety.

BACKGROUND

Endoscopes are catheter-based devices that can be used to perform minimally-invasive procedures (e.g., surgery). Endoscopes can be designed to permit a health care practitioner such as a physician to visualize and/or treat the internal tissues of a patient through a small incision in the skin. An endoscope can include a light source and a camera. Fiberscopes (or fiber-optic endoscopes) can include illumination fibers or light guides that direct light to illuminate the field of view. Endoscopes can include imaging fiber bundles to transfer the image of an illuminated area to the camera. In diagnostic arthroscopy, after introducing the device into the patient's joint, a physician can shine light into that joint. The camera provides an image of the joint, which is then viewed on a video monitor. By viewing the joint of interest through the device, the physician does not need to make a large incision. Sterile fluid can be used to expand the joint, which increases visibility in the joint area and makes it easier for the physician to work. These single-port diagnostic procedures have been performed in a doctor's physician and "walk in" or ambulatory surgery centers, e.g., using a 2.0 mm fiber optic arthroscope.

FIELD

The present disclosure relates to endoscopy systems. More particularly, some embodiments herein relate to methods and systems comprising one or more of piezoelectric elements, stylets, and hooked blades. In some embodiments, the endoscopy systems are useful for orthopedic procedures. In some embodiments, the endoscopy systems are useful for arthroscopic procedures.

SUMMARY

Some aspects include an endoscopy system comprising a sheath, an image sensor, an illuminating element, a working channel and a piezoelectric element. The sheath can comprise a lumen and an opening at a distal-most end of the sheath. A distal portion of the sheath can be deformable. The image sensor can be disposed within the lumen of the distal portion of the sheath. The illuminating element can be disposed within the lumen adjacent to the image sensor. The working channel can be disposed within the lumen. The working channel can comprise a distensible portion that extends past at least a portion of the image sensor. The piezoelectric element can be sized to fit within the working channel. The piezoelectric element can be coupled to a working tip. The piezoelectric element can be configured to move the working tip when electricity is applied to the piezoelectric element. The working tip can be configured to puncture a tissue when the working tip is moved a result of electricity being applied to the piezoelectric element. In some embodiments, the working tip has a diameter within the range of 0.1 mm to 1.0 mm.

Some aspects include an endoscopy system for performing a procedure on a connective tissue. The system can comprise a sheath, an image sensor, an illuminating element, a working channel, and a hooked blade. The sheath can comprise a lumen. A distal-most end of the sheath can comprise an opening. A distal portion of the sheath can be deformable. The image sensor can be disposed within the lumen of the distal portion of the sheath. The illuminating element can be disposed within the lumen and adjacent to the image sensor. The working channel can be disposed within the lumen and can comprise a distensible portion that extends past at least a portion of the image sensor. The hooked blade can be sized to fit within the working channel. The hooked blade can comprise a convex distal-facing surface and a concave proximal-facing cutting surface. The convex distal-facing surface can have a smoothness sufficient to atraumatically distend the distensible portion of the working channel as the hooked blade is advanced distally past the image sensor. In some embodiments, the convex distal facing surface has a radius of curvature within the range of between 0.1 mm and 1.0 mm. In some embodiments, the concave proximal facing cutting surface has a radius of curvature within the range of 0.1 mm to 1.0 mm.

Some aspects include a stylet configured to perform an arthroscopic procedure with an endoscopy system that comprises a sheath comprising a lumen, a distal-most end of the sheath comprising an opening, a distal portion of the sheath being deformable; an image sensor disposed within the lumen of the distal portion of the sheath; an illuminating element disposed within the lumen adjacent to the image sensor; and a working channel disposed within the lumen, the working channel comprising a distensible portion that extends past at least a portion of the image sensor. The stylet can be sized to fit within the working channel. The stylet can have a rigidity sufficient to bend the distal portion of the sheath when the stylet is advanced distally past at least a portion of the image sensor.

Some aspects include a method of performing a procedure with the endoscopy system of any one of the preceding paragraphs. The method can include introducing the endoscopy system through an incision in a skin of a patient to reach the tissue of the patient, wherein said tissue is an internal tissue of the patient; puncturing the tissue of the patient with the working tip; and withdrawing the endoscopy system from the patient through the incision.

Some aspects include a method of performing a procedure with the endoscopy system of any one of the preceding paragraphs. The method can include introducing the endoscopy system through an incision in a skin of a patient to reach the connective tissue of the patient, wherein the connective tissue is an internal tissue; incising the connective tissue with the hooked blade; and withdrawing the endoscopy system from the patient through the incision.

Some aspects include a method of preparing the stylet of any one of the preceding paragraphs for use with an arthroscopic procedure with the endoscopy system. The method can include bending a distal portion of the stylet to a desired shape; and inserting the distal portion of the stylet into the working channel of the endoscopy system.

BRIEF DESCRIPTION OF THE DRAWINGS

FIG. 6 is a schematic diagram of an endoscopy system comprising a hooked blade in accordance with some embodiments herein.

FIG. 7A is a schematic diagram of an endoscopy system comprising a hooked blade in accordance with some embodiments herein showing the endoscope inserted under a carpal ligament with the hooked blade housed within the endoscope.

FIG. 7B is a schematic diagram of an endoscopy system comprising a hooked blade in accordance with some embodiments herein showing the endoscope inserted under a carpal ligament with the hooked blade deployed from within the endoscope.

FIG. 7C is a schematic diagram of an endoscopy system comprising a hooked blade in accordance with some embodiments herein showing the incised carpal ligament after the endoscope has been drawn away from under the carpal ligament with the hooked blade deployed from the endoscope.

FIG. 8A is a schematic diagram of a stylet and sheath for performing an arthroscopic procedure with an endoscopy system in accordance with some embodiments herein.

FIG. 8B is a schematic diagram of a stylet inserted into the stylet working channel of the endoscope to reposition the distal tip of the sheath.

DETAILED DESCRIPTION

Figure 1:
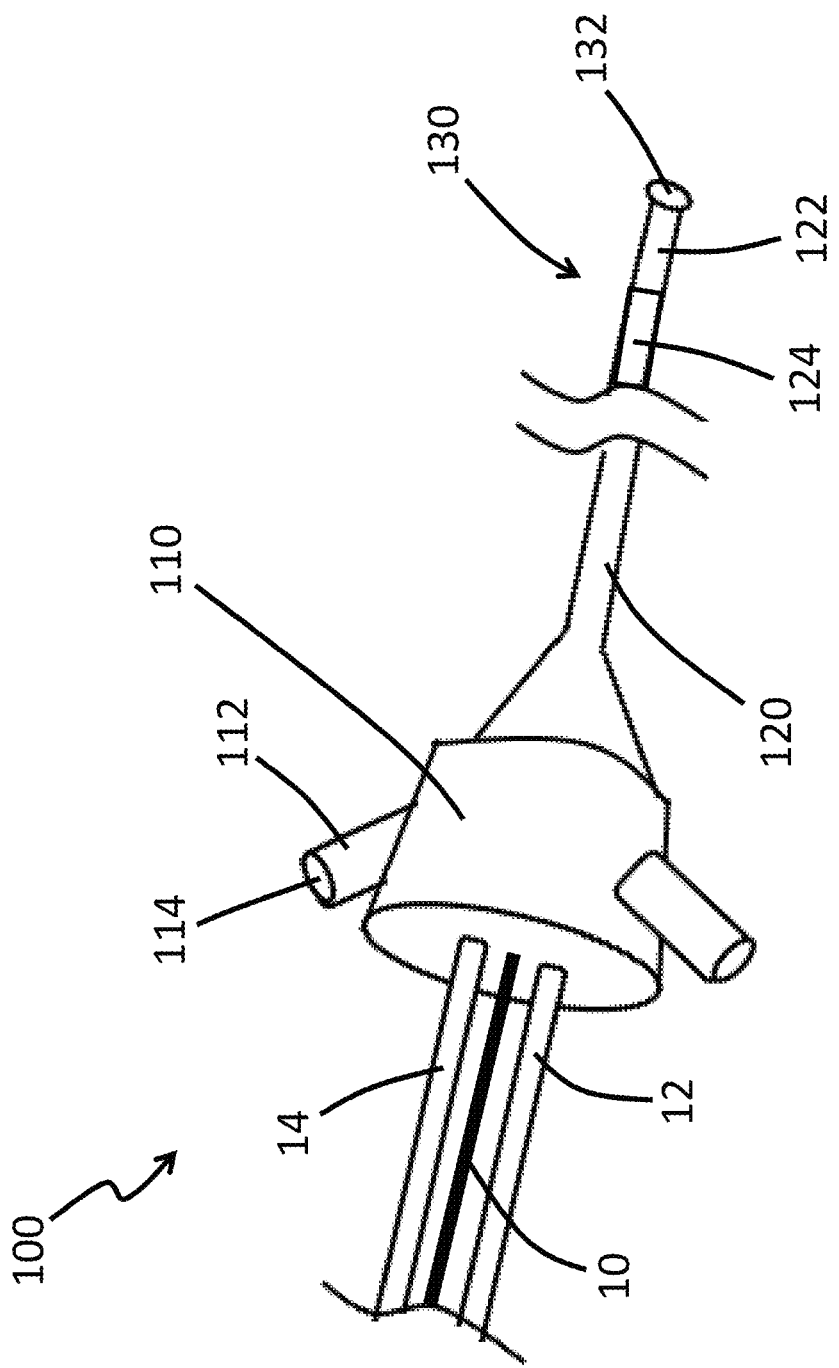
FIG. 1 is a schematic diagram of an endoscopy system in accordance with some embodiments herein.

In some embodiments, endoscopy systems are described. In some embodiments, an endoscopy system comprises a piezoelectric element coupled to a working tip. The piezoelectric element can drive the working tip to puncture a tissue of a patient such as bone. Accordingly, in some embodiments, the endoscopy system can be useful for performing microfracture surgery using a single endoscope and a single incision.

In some embodiments, an endoscopy system comprises a hooked blade that can be distended from a working channel. Once distended, the hooked blade can incise a connective tissue. In some embodiments, the shaft of the endoscopy system can act as a tissue expander as it is slid alongside the median nerve, and then the hooked blade can be distended to incise a carpal ligament. Accordingly, in some embodiments, the endoscopy system can be useful for carpal tunnel surgery that utilizes only a single endoscopy system, and a single incision.

In some embodiments, a stylet for performing an arthroscopic procedure is described. Certain joints such as the hip or the back of the knee can be challenging for conventional endoscopy systems to visualize. An operator can alter the stiffness of the shaft of an endoscopy system by interchanging curved stylets in the shaft. The stylets can be configured to be advanced through a working channel of an endoscopy system as described herein. Accordingly, in some embodiments, an operator can use the stylet or stylets to adjust the tip location. The field of illumination and/or image capture can thus be altered by the use of the stylets. Thus, in some embodiments the stylet or stylets can facilitate visualization of difficult-to-reach locations.

Various exemplary aspects of the described technology are illustrated in the Figures and discussed herein, which are presented to enable the manufacture and use of various aspects and examples of that technology. Descriptions of specific materials, techniques, and applications are provided as examples. No limitation on the scope of the technology and of the claims that follow is to be imputed from the drawings, the examples, or the discussion below.

Endoscopy Systems

In some embodiments, endoscopy systems are described. It is understood herein that when the term "endoscope" is mentioned herein (including variations of this root term), an endoscopy system is also expressly contemplated. Additionally, it is understood that when "endoscopy systems" (including variation of this root term) are mentioned herein, endoscopy systems comprising, consisting of, or consisting essentially of only a single endoscope are expressly contemplated, but that an endoscopy system is not necessarily limited to only a single endoscope.

The endoscopy system in accordance with some embodiments can include one or more working channels that extend within the lumen of the sheath. For example, the endoscopy system can include a working channel that is sized to allow a tool to be inserted into the working channel. The working channel can be configured to allow a tool inserted into the working channel to be advanced along the working channel to reach a distal end of the endoscope. In some embodiments, the working channel can have an opening at a distal end of the working channel, thereby allowing a distal portion of the tool to exit the distal end of the endoscope. A distal portion of the working channel can be distensible and a longitudinally overlapping portion of the outer sheath can also be deformable, allowing the profile of the endoscope to expand as a tool within the working channel moves distally past an element (e.g., image sensor) within the lumen of the endoscope.

The endoscopy system in accordance with some embodiments can include additional working channels such as, for example, to allow a second tool to reach the distal end of the endoscope, a fluid flushing channel, a fluid suction channel, and one or more stylet working channels. The endoscopy system can allow a single endoscope to be used for visualizing of the tissue (e.g., via the image sensor and illuminating element), expanding the tissue (e.g., via the fluid flushing channel), and performing a surgical procedure on the tissue (e.g., via the working channel).

In some embodiments, the endoscopy system has an outer sheath comprising a lumen and an opening at the distal-most end of the sheath. The endoscopy system can include an image sensor (for example, a camera) and an illuminating element that are disposed within the lumen of the sheath. The illuminating element can be configured to pass light through the opening at the distal-most end of the sheath to illuminate a field of view. The image sensor can be adapted to detect light reflected from the tissue illuminated by the illuminating element, thereby allowing a user to visualize tissue at the distal-most end of the endoscope. In some embodiments, the endoscopy systems are single-use endoscopy systems for use in surgical procedures.

In some embodiments, a laser provides light to the illuminating element of the endoscopy system. Without being limited by theory, it is contemplated that a laser can provide enough light via a single light guide fiber to illuminate a field of view. In some embodiments, the laser provides light via a single light guide fiber. As such, in some embodiments, the use of a laser, and/or a laser and a single light guide fiber can yield an endoscopy system with a smaller diameter, thus minimizing invasiveness of the endoscopy system.

FIG. 1 depicts a generalized endoscope 100 in accordance with some embodiments. The endoscope 100 can include a hub 110, which remains outside the patient's body. The hub 110 can be used by the operator to manipulate the endoscope 100, as described herein. An elongated, flexible shaft 120 can extend from that hub 110. The shaft 120 can be inserted into the patient's body. The shaft 120 can connect the hub 110 to a distal tip 130 of the endoscope 100. The shaft 120 can have an opening 132 at the distal tip 130 of the endoscope 100. The shaft 120 can be hollow or include one or more lumens. The opening 132 can provide a path for the interior space of the shaft 120 (or the interior space of a lumen within the shaft) to communicate with the outside environment. For example, the opening 132 can allow the interior space of the shaft 120 to communicate with an internal cavity of a patient when the shaft 120 is inserted through an incision in the skin of the patient.

The hub 110 can include one or more ports 112. As described herein, an item (e.g., tool, flushing fluid) can be inserted into a proximal opening 114 of the port 112, advanced along the interior of the shaft 120, and passed through the opening 132 at the distal end 130 of the shaft 120. The hub 110 can be adapted to receive a guidewire 10. For example, in the illustrated embodiment, the endoscope 100 is mounted onto a guidewire 10 in an over-the-wire configuration. The endoscope 100 can be mounted onto a guidewire 10 in a rapid exchange configuration. The endoscope 100 can include data communication lines 12 and/or power lines 14. The hub 110 can be configured to allow data communication lines 12 and/or power lines 14 to extend out of the hub 110. The data communication line 12 can transmit data (e.g., image sensor data) to an electronic device (e.g., display screen). The power line 14 can provide power to electronics housed within the hub 112 or at another location of the endoscope 100.

The shaft 120 can include an expandable portion 122. The expandable portion 122 can be adapted to reversibly expand. The expandable portion 122 can be configured to expand radially to allow items that have a large profile to push distally past other components of the endoscope 100 that are located at the expandable portion 122 of the shaft 120. For example, the expandable portion 122 can surround a camera lens that occupies a large size profile. The expandable portion 122 can expand to allow tools to navigate distally past the camera lens.

The shaft 120 can include a rigid portion 124. The rigid portion 124 can be adapted so that it does not reversibly expand. The rigid portion 124 can longitudinally align with portions of the shaft 120 that need not expand to allow a large profile item to advance distally toward the opening 132. For example, the rigid portion 124 can surround fiber optic fibers, electrical cords, or other low-profile items that do not require the shaft 120 to radially expand to allow a tool to advance past these low-profile items.

In some embodiments, the distal portion of the shaft 120 that is inserted into the patient can have an outer diameter of about 2 mm. In some embodiments, the outer diameter of the shaft is about: 0.5 mm, 0.6 mm, 0.8 mm, 1.0 mm, 1.5 mm, 2.0 mm, 3.0 mm, 4.0 mm, or 5.0 mm, including ranges between any two of the listed values. In some arrangements, the outer diameter of the shaft 120 is between the range of 0.5 mm to 5.0 mm, 1.0 mm to 4.0 mm, 2.0 mm to 3.0 mm, or 1.5 mm to 2.5 mm.

Figure 2B:
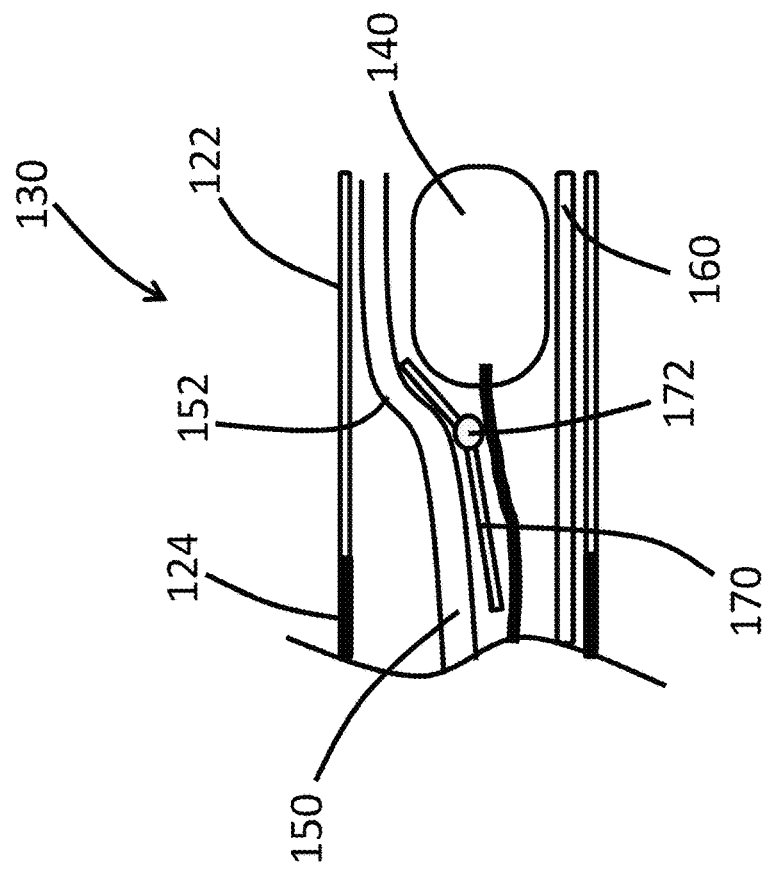
FIG. 2B is a cross-sectional side view of a distal tip of an endoscope comprising a working channel in accordance with some embodiments herein.
Figure 2A:
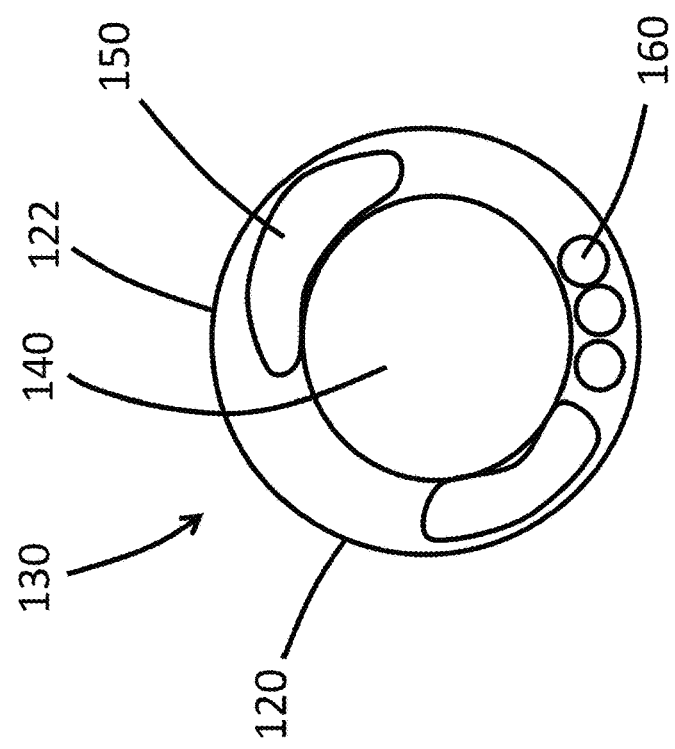
FIG. 2A is an end view of a distal tip of an endoscope comprising a working channel in accordance with some embodiments herein.

FIG. 2A shows an end view of a non-limiting, illustrative embodiment of a distal tip 130 of the endoscope 100. The expandable portion 122 of the shaft 120 can surround an image sensor 140. One more working channels 150 can be disposed within the lumen of the shaft 120. The working channels 150 can be sized to allow an item to be passed through the working channel 150 to reach the distal tip 130 of the endoscope 100. In the illustrated embodiment, the distal tip 130 includes two working channels 150 that are disposed radially outward of the image sensor 140. In some embodiments, the distal tip 130 includes only one working channel 150. In some arrangements, the endoscope 100 includes three or more working channels 150. As discussed herein, the working channel 150 can include a distensible portion that can reversibly deform to allow the cross-sectional area of the lumen of the working channel 150 to increase.

With continued reference to FIG. 2A, the distal tip 130 can include illumination fibers 160. In the illustrated embodiment, the distal tip 130 includes three illumination fibers 160. In some embodiments, the distal tip 130 includes only one illumination fibers 160. In some arrangements, the endoscope 100 includes two or more than three illumination fibers 160. In at least one embodiment, the endoscope 100 can include only one illumination fiber 160 and that single illumination fiber 160 is couple to a powerful laser light source, thereby allowing the single illumination fiber 160 to provide enough light to adequate illuminate the tissue space for imaging with the image sensor 140.

FIG. 2B shows a cross-sectional side view of another embodiment of a distal tip 130. The distal tip 130 includes a ramp 170 that is adapted to guide the working channel 150 around the image sensor 140. The ramp 170 can be arranged so that an item (e.g., tool) that is advanced within the working channel 150 past the image sensor 140 does not impact or alter the orientation of the image sensor 140. The ramp 170 can protect the image sensor 140 from being knocked out of proper alignment when an item within the working channel 150 advances past the image sensor 140. In the illustrated embodiment, the distal tip 130 has only one working channel 150. However, the endoscope 100 can include additional working channels 150 and ramps 170 that protect the sensor 140 from being knocked out of alignment. In some configurations, the ramp 170 can be anchored to the rigid portion 124 of the shaft 120. For example, the ramp 170 can include a pin 172 that is connected to the rigid portion 124 by a strut (not shown).

As discussed, the working channel 150 can include a distensible portion 152 that longitudinally aligns with the expandable portion 122 of the shaft 120. As an item (e.g., tool) is advanced distally along the working channel 150, the ramp 170 directs the item away from the image sensor 140, thereby protecting the alignment of the image sensor 140. As the item passes by the image sensor 140, the distensible portion 152 of the working channel 150 radially expands to allow the item to pass by the image sensor 140 without disrupting the position of the image sensor 140. The radial expansion of the distensible portion 152 of the working channel 150 can cause the expandable portion 122 of the shaft 120 to radially expand to accommodate the profile of the item passing by the image sensor 140. Once the item in the working channel 150 is no longer longitudinally aligned with the image sensor 140, the distensible portion 152 and the expandable portion 122 can deform back to a low-profile configuration.

Additional information about endoscopes, including endoscopes and features of endoscopes suitable in accordance with some embodiments herein, can be found in International Application Publication No. WO 2017/027299, entitled "ENDOSCOPE WITH VARIABLE PROFILE TIP," and U.S. Patent Application Publication No. 2017/0035277, entitled "ENDOSCOPE WITH VARIABLE PROFILE TIP," each of which is hereby incorporated by reference in its entirety.

Endoscopy Systems Comprising Piezoelectric Elements and Methods of Using

In some embodiments, the endoscopy system comprises a piezoelectric element. In some embodiments, the piezoelectric element can be adapted to perform an arthroscopic procedure (e.g., microfracture) on a tissue of a patient. The piezoelectric element can be sized to fit within a working channel of the endoscope. The piezoelectric element can be coupled to a working tip and configured to move the working tip when electricity is applied to the piezoelectric element.

Microfracture surgery is a kind of arthroscopic surgery in which cartilage can be repaired by creating very small fractures in the underlying bone. Without being limited by theory, it is believed that blood and cells can enter the fractures, and cartilage can form as a result of the entry of these substances. In some embodiments, an endoscopy system comprising a piezoelectric element is configured for microfracture surgery. The piezoelectric element can be suited to create the very small bone fractures for a microfracture procedure.

Figure 3A:
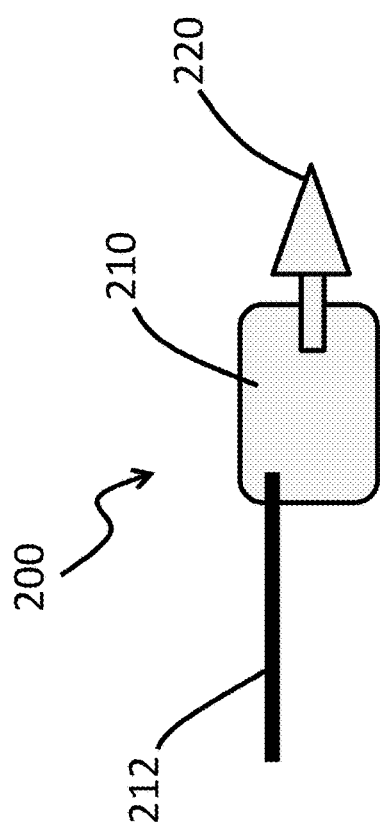
FIG. 3A is a schematic diagram of a piezoelectric element directly coupled to a working tip in accordance with some embodiments herein.
Figure 3B:
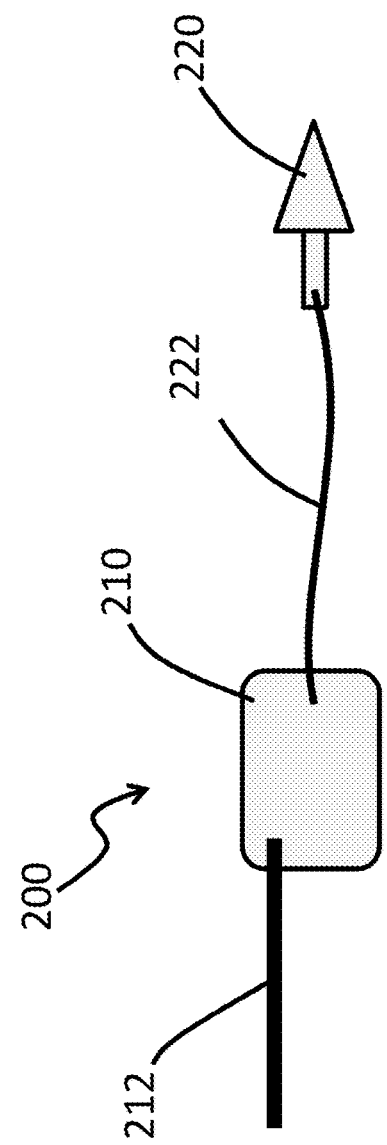
FIG. 3B is a schematic diagram of a piezoelectric element coupled to a working tip by an intermediate wire in accordance with some embodiments herein.

FIG. 3A depicts a non-limiting, illustrative embodiment of a piezoelectric element 200. The piezoelectric element 200 can be used with the endoscope 100. In some embodiments, the piezoelectric element 200 is sized to fit within the working channel 150 of the endoscope. The piezoelectric element 200 can include a transducer 210 and a power cable 212 that provides electricity to the transducer 210. The piezoelectric element 200 can include a working tip 220. The piezoelectric element 200 can be configured so that the working tip 220 moves when electricity is applied to the transducer 210. As shown in FIG. 3A, in certain arrangements, the working tip 220 is coupled directly to the transducer 210 (without any intervening elements). In certain arrangements, the transducer 210 is coupled to the working tip 220 via an intervening wire 222, as shown in FIG. 3B. The intervening wire 222 can be sufficiently rigid to transmit a compressive force from the transducer 210 to the working tip 220. In some embodiments, the intervening wire comprises a metal (e.g., surgical steel, nitinol), a polymeric material, a ceramic, or combinations thereof.

The working tip 220 can be configured to puncture a tissue (e.g., bone) when the working tip 220 is moved as a result of electricity being applied to the piezoelectric element 200. In some embodiments, the working tip 220 is configured to puncture a bone when moved by the piezoelectric element 200, thereby allowing the piezoelectric element 200 to be used to perform a microfracture procedure on a patient. The piezoelectric element 200 can be configured to exert a force, for example at least about a 15N force, on the working tip 220. In some embodiments, the piezoelectric element 200 can be configured to exert a force of about: 1N, 15N, 30N, 50N, 100N, 200N, 500N, including ranges between any two of the listed values. The working tip 220 can have a tip angle of between about 5° and 10°, thereby allowing the working tip 220 to puncture cortical bone when the force is applied to the working tip 220. In some embodiments, the working tip 220 can have a tip angle of about: 1°, 2°, 5°, 7°, 10°, 15°, 20°, or 45°, including ranges between any two of the listed values. In some embodiments, the working tip 220 is positioned in parallel or substantially in parallel with the image sensor 140. As such, the working tip 220 can be facing the same angle as the image sensor. For example, both the working tip 220 and image sensor 140 can be forward facing.

Figure 4A:
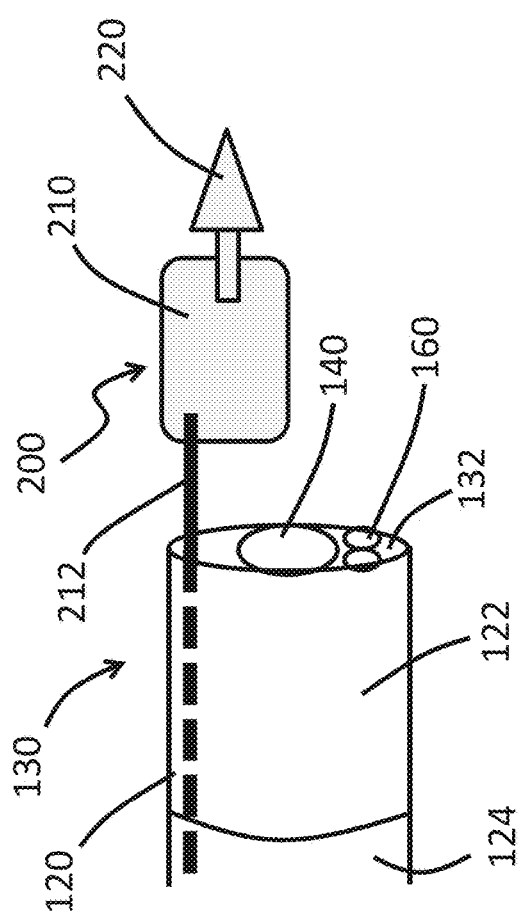
FIG. 4A is a partial side view of a distal tip of an endoscope comprising a piezoelectric element in accordance with some embodiments herein.
Figure 4B:
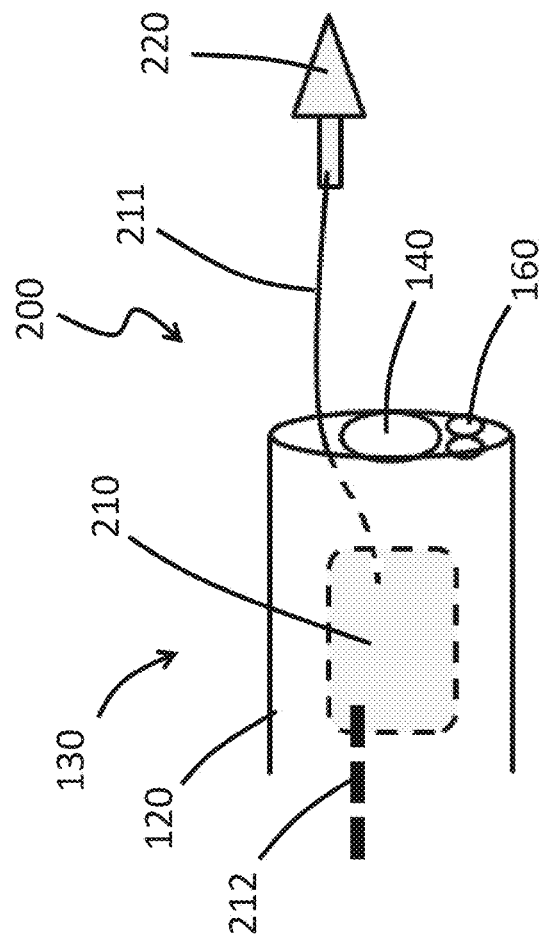
FIG. 4B is a partial side view of a distal tip of an endoscope comprising a piezoelectric element in accordance with some embodiments herein.

FIGS. 4A and 4B illustrate different arrangements in which the piezoelectric element 200 can be used with the endoscope 100. Although the working channel 150 is not shown in FIGS. 4A and 4B, the piezoelectric element 200 can be inserted within a working channel 150 and advanced to the distal tip 130 of the sheath 120 of the endoscope 100. The working channel 150 (not shown) can include a distensible portion 152 (shown in FIG. 2B) that longitudinally aligns with the deformable portion 122 of the sheath 120, thereby allowing the sheath 120 to radially expand to allow at least a portion of the piezoelectric element 200 to be distally advanced past the image sensor 140 without disrupting the alignment of the image sensor 140, as described herein.

Referring to FIG. 4A, in some embodiments, the piezoelectric element 200 comprises a transducer 210 that is disposed distally of the image sensor 140 when the working tip 220 is positioned distally beyond the opening 132 at the distal tip 130 of the sheath 120. In some embodiments, the transducer and the working tip are both disposed distal of the image sensor when the working tip extends distally beyond the opening at the distal-most end of the sheath. In some embodiments, the piezoelectric element 200 can include a wire 211 or similar low-profile connector (e.g., strip, ribbon) that connects the transducer 210 to the working tip 220. As shown in FIG. 4B, in some arrangements, the transducer 210 is disposed proximally to the image sensor 140 when the working tip 220 is positioned distally beyond the opening 132 at the distal tip 130 of the sheath 120. In some embodiments, the piezoelectric element 200 includes a wire 211, and the transducer 210 and the working tip 220 are both disposed distal of the image sensor 140 when the working tip 220 extends distally beyond the opening 132 at the distal tip 130 of the sheath 120.

Figure 5:
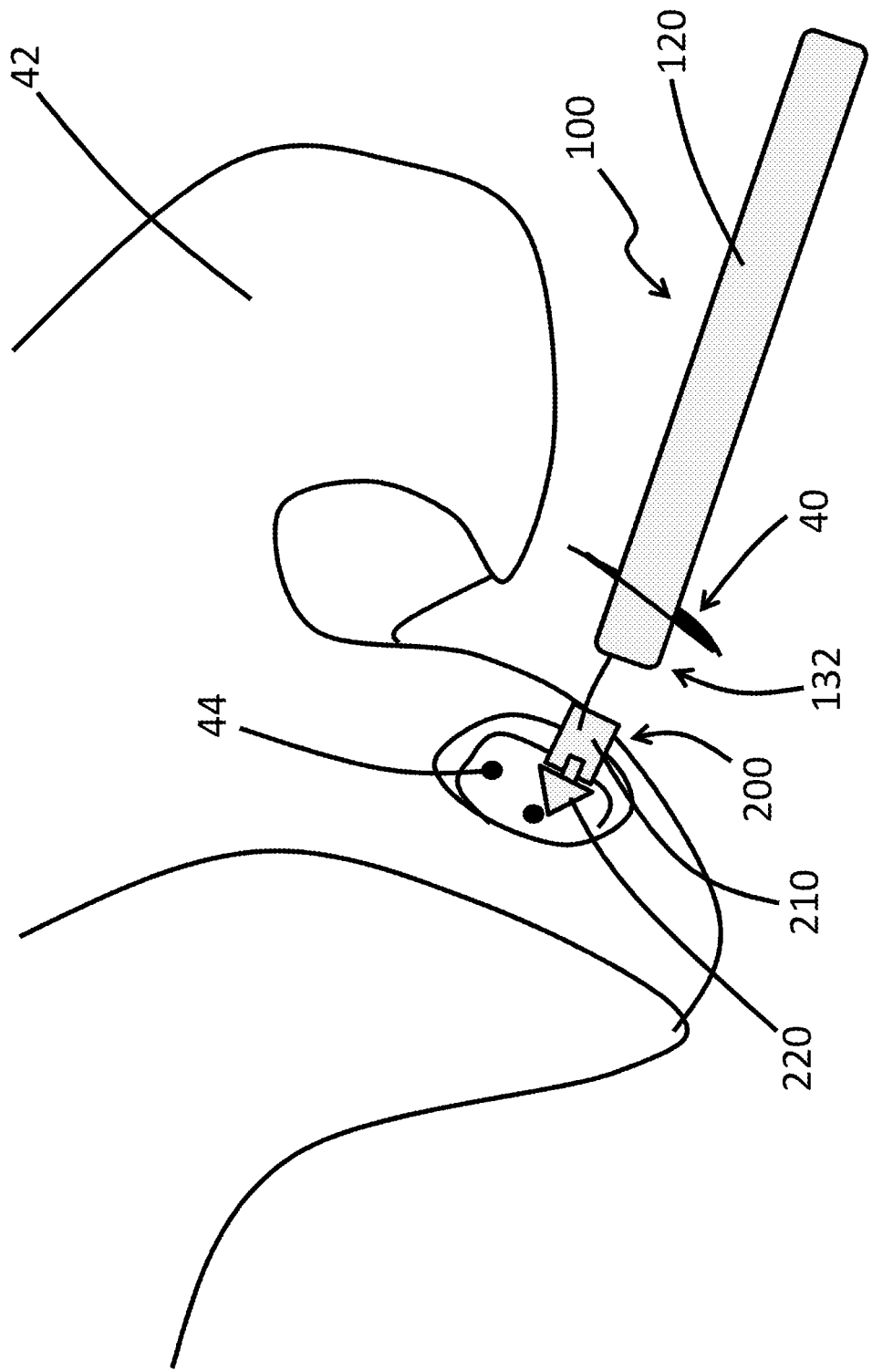
FIG. 5 is a schematic diagram of a microfracture procedure being performed on a bone with an endoscopy system comprising a piezoelectric element in accordance with some embodiments herein.

FIG. 5 illustrates a microfracture procedure being performed with an embodiment of the endoscope 100 having a piezoelectric element 200. In some embodiments, the sheath 120 is inserted through an incision 40 in the skin of a patient to position the distal tip 132 of the sheath 120 near a bone 42 of the patient. As discussed, the endoscope 100 can include an image sensor 140 (shown in FIGS. 4A and 4B) and an illumination element 160 that are configured to allow a user (e.g., physician) to visualize the target site of bone 42 on which the microfracture procedure is to be performed. The piezoelectric element 200 is advanced distally along the sheath 120 to bring the working tip 220 near the target site of the bone 42. As described above, the endoscope 100 can be configured to allow the working tip 220 to pass by the image sensor 140 without disturbing the alignment of the image sensor 140. In the illustrated embodiment, the working tip 220 is directly coupled to the transducer 210 of the piezoelectric element 200, and both the transducer 210 and the working tip 220 are extended distally beyond the image sensor 140 and outside of the sheath 120 of the endoscope 100. In some methods, other arrangements of the piezoelectric element 200 can be used to perform the microfracture procedure. The piezoelectric element 200 is energized to move the working tip 220 and create microfractures or holes 44 in the bone 42, thereby performing a microfracture procedure on the bone 42. In some embodiments, the microfracture procedure is performed using only a single endoscopy system 100.

In some embodiments, the endoscope 100 having a piezoelectric element 200 can be used to treat (e.g. biopsy) a target tissue (e.g., liver) in a procedure other than microfracture surgery. In some embodiments of the method, the sheath 120 is inserted into a patient and the distal tip 132 of the sheath 120 is positioned near a target tissue of the patient, for example tissue comprising, consisting essentially of, or consisting of bone. As discussed, the endoscope 100 can include an image sensor 140 and an illumination element 160 that are configured to allow a user (e.g., physician) to visualize the target tissue on which the procedure is to be performed. The piezoelectric element 200 is advanced distally along the sheath 120 to bring the working tip 220 near the target tissue. As described above, the endoscope 100 can be configured to allow the working tip 220 to pass by the image sensor 140 without disturbing the alignment of the image sensor 140. In certain methods, the working tip 220 is directly coupled to the transducer 210 of the piezoelectric element 200, and both the transducer 210 and the working tip 220 are extended distally beyond the image sensor 140 and outside of the sheath 120 of the endoscope 100. The piezoelectric element 200 is energized to move the working tip 220 and drive the working tip into the target tissue. In some methods, the piezoelectric element 200 is adapted to perform a tissue-puncturing procedure on the target tissue. For example, the endoscope 100 comprising the piezoelectric element 200 could be used to lacerate or biopsy the target tissue. In some methods, the piezoelectric element 200 is adapted to indent or otherwise deform the target tissue without puncturing the target tissue.

Endoscopy Systems for Performing a Procedure on Connective Tissue, and Methods of Using Such Endoscopy Systems For some procedures, it can be advantageous to incise a connective tissue. For example, in carpal tunnel surgery, incising the transverse carpal ligament can be incised, so as to relieve symptoms of carpal tunnel syndrome. In some embodiments, an endoscopy system is configured for carpal tunnel surgery.

Referring to FIG. 6, in some embodiments, the endoscopy system 100 comprises an image sensor 140, an illuminating element 160, and a working channel 150 that allows the endoscope 100 to be the only endoscope 100 needed to visualize and perform a procedure on a connective tissue of a patient. The endoscopy system 100 can include a sheath 120 having a lumen and an opening 132 at the distal tip 130 of the sheath 120. An image sensor 140 and illuminating element 160 can be disposed within the lumen of the sheath 120. At least the portion 122 of the sheath 120 that longitudinally aligns with the image sensor 120 can be deformable, allowing the sheath 120 to deform from a low-profile configuration to a high-profile configuration. The endoscopy system 100 can include a working channel 150 that extends within the lumen of the sheath 120. The working channel 150 can include a distensible portion 152 (shown in FIG. 2B) that can deform from a low-profile configuration to a high-profile configuration. The distensible portion 152 of the working channel 150 can be longitudinally aligned with the deformable portion 122 of the sheath 120 and the image sensor 140, thereby allowing the endoscope 100 to expand as a tool within the working channel 150 is advanced distally past the image sensor 140.

The endoscopy system 100 can include a hooked blade 300 that is sized to fit within the working channel 150 of the endoscope 100. The hooked blade can be made, for example, of steel, titanium, surgical grade steel, a polymeric material, a ceramic, or a combination of these. The hooked blade 300 can have a convex distal-facing surface 302 and a concave proximal-facing cutting surface 304. The convex distal-facing surface 302 can be configured to atraumatically distend the distensible portion 152 (shown in FIG. 2B) of the working channel 150 as the hooked blade 300 is urged distally past the image sensor 140. The convex distal-facing surface 302 can have a radius of curvature between 2 mm and 4 mm. In some embodiments, the convex distal-facing surface 302 can have a radius of curvature of about: 0.5 mm, 1 mm, 2 mm, 3 mm, 4 mm, 6 mm, including ranges between any two of the listed values. The concave proximal-facing cutting surface 304 can have a radius of curvature between 0.5 mm and 1.0 mm. In some embodiments, the concave proximal-facing cutting surface 304 can have a radius of curvature of about: 0.1 mm, 0.2 mm, 0.5 mm, 1.0 mm, 2.0 mm, 4.0 mm, including ranges between any two of the listed values.

As described previously, the endoscope 100 can be configured so that the hooked blade 300 does not disturb the alignment of the image sensor 140 as the hooked blade 300 is urged distally past the image sensor 140. For example, the endoscope 100 can include a ramp 170 (shown in FIG. 2B) that guides the working channel 150 past the image sensor 140.

FIGS. 7A-7C illustrate a method of performing a procedure on connective tissue (e.g., incision of a carpal ligament) with the endoscope 100 that includes a hooked blade 300. Referring to FIG. 7A, the distal tip 132 of the endoscope 100 can be inserted through an incision in the skin and advanced along the medial nerve 50, passing underneath a carpal ligament 52 of a patient. The sheath 120 can act as a tissue expander as the endoscope is advanced along the medial nerve. The hooked blade 300 can be housed within the sheath 120 as the distal tip 130 traverses underneath the carpal ligament 52. After the distal tip 132 of the sheath clears the distal edge of the carpal ligament 52, the hooked blade 300 can be distally advanced along the working channel 150 until the hooked blade 300 exits the opening 132 at the distal tip 130 of the sheath 120 (see FIG. 7B). The hooked blade 300 can be positioned so that the convex proximal-facing cutting surface 304 is disposed distally beyond the distal tip 130 of the sheath 120. The endoscope 100 and hooked blade 300 can then be proximally retracted together, pulling the convex proximal-facing cutting surface 304 against and through the carpal ligament 52, thereby incising the carpal ligament 52 (see FIG. 7C). As shown by the dashed line in FIG. 7C, an incision 54 can be made in the carpal ligament 52 with the hooked blade 300. In some embodiments, the method is performed using only a single endoscopy system 100.

Stylets

In some embodiments, one or more stylets 400 assist in the positioning of the distal tip 130 of the endoscopy system 100 as described herein. FIG. 8A shows the stylet 400 can be sized to fit within a stylet working channel 155 disposed within the sheath 120 of the endoscope. FIG. 8B shows the distal tip 130 of the sheath 120 can be deflected or repositioned when the stylet 400 is inserted into the stylet working channel 155. The stylet working channel 155 can extend past at least a portion of the image sensor 140 of the endoscope 100. The stylet 400 can have a rigidity sufficient to bend the distal tip 130 of the sheath 120 when the stylet 400 is advance distally past at least a portion of the image sensor 140. The endoscope 100 can include a guide means (e.g., ramp) that guides the stylet working channel 155 past the image sensor 140 so that insertion of the stylet 400 does not disturb the alignment of the image sensor 140 relative to the illumination element 160, although both components can be deflected together when the distal tip 130 when the stylet 400 is inserted in the stylet working channel 155. Thus, the stylet 400 can be used to reposition the distal tip 130 of the sheath 120 without knocking the image sensor 140 out of alignment with the illumination element 160, allowing the image sensor 140 to image the tissue in the illumination field after the stylet 400 has repositioned the distal tip 130.

In some embodiments, the stylet 400 is malleable, allowing an operator (e.g., physician) to reform the stylet 400 to a desired shape. The stylet can be made for example, from metal (e.g., steel, titanium, nitinol), a polymeric material, a ceramic, or a combination of these. In some embodiments, the stylet is made from a nitinol shape memory alloy. In certain arrangements, the stylet 400 can be reformed by hand and without the use of a tool. The stylet 400 can be one of a plurality of stylets, thereby allowing a user to select the stylet most suitable for the anatomy of the patient. In some arrangements, the stylet 400 is advanced into the stylet working channel 155 before the sheath 120 is inserted into the patient. In some embodiments, the sheath 120 is advanced into the patient without the stylet 400 in the stylet working channel 155. The stylet 400 can be advanced into the stylet working channel 155 after the sheath 120 has been placed inside of the patient.

In some embodiments, the endoscope 100 includes a stylet working channel 155 and one or more working channels 150. For example, the endoscope 100 can include a stylet working channel 155 and a working channel 150 sized to receive a piezoelectric element 200. The stylet 400 can be inserted into the stylet working channel 155 to properly position the distal tip 130 of the sheath 120 for a microfracture procedure using a piezoelectric element 200 delivered to the target tissue site through a working channel 150, as described previously.

EXAMPLES

Example 1

An endoscopy system for performing a microfracture procedure includes a deformable outer sheath that circumferentially surrounds an image sensor, an illuminating element, and a piezoelectric element coupled to a working tip. The piezoelectric element is housed within a working channel having a distensible portion longitudinally aligned with the image sensor. The piezoelectric element is configured to apply a 15 N force on the working tip. The working tip is made of tungsten, has a diameter of 0.1 mm, and has sufficient hardness to puncture cortical bone when the piezoelectric element is energized to apply a 15 N force at the distal end of the working tip.

Example 2

The endoscopy system of Example 1 is inserted through a 2 mm incision in a skin of a patient and advanced into a knee joint of the patient. The piezoelectric element is advanced distally along the working channel to extend the working tip distally beyond the outer sheath of the endoscope. The working tip is positioned near the bone surface. The piezoelectric element is energized to move the working tip, causing the working tip to puncture the bone. As such, a microfracture procedure is performed using only a single endoscope.

Example 3

An endoscopy system for incising a carpal ligament includes a deformable outer sheath that circumferentially surrounds an image sensor, an illuminating element, and a working channel having a distensible portion that longitudinally aligns with the image sensor. The endoscopy system further includes a hooked blade having a convex distal-facing surface that has a radius of curvature of 2 mm. The hooked blade has a concave proximal-facing surface that has a radius of curvature of 1.2 mm.

Example 4

The endoscopy system of Example 3 is inserted through a 2 mm incision in a skin of a patient and advanced along the median nerve underneath the carpal ligament. The hooked blade is advanced distally beyond the outer sheath. The hooked blade is held fixed relative to the outer sheath as the outer sheath is withdrawn proximally across the carpal ligament, thereby incising the carpal ligament with the concave proximal-facing surface of the hooked blade. As such, carpal tunnel surgery is performed using only a singly endoscope.

Example 5

A stylet for use with the endoscopy system of the present disclosure is sized to fit within a working channel that extends through the lumen of an outer sheath of the endoscope. The stylet has sufficient rigidity to bend the distal portion of the outer sheath to a desired position to assist with an arthroscopic procedure.

Example 6

The stylet of Example 5 is inserted into a working channel of an endoscope and advanced through a 2 mm incision in a skin of a patient for imaging of the hip. The curvature of the stylet disposes the distal tip of the endoscope in a desired position for imaging of the hip.

One skilled in the art will appreciate that, for processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. For example, "about 5", shall include the number 5. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

For methods disclosed herein, such as methods of performing a procedure, corresponding uses are also expressly contemplated. For example, for methods of performing a procedure with an endoscopy system, endoscope, or stylet, corresponding uses of the subject endoscopy system, endoscope, or stylet, for the procedure are also contemplated.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. An endoscopy system comprising:
   a sheath comprising a lumen and an opening at a distal-most end of the sheath, a distal portion of the sheath being deformable;
   an image sensor disposed within the lumen of the distal portion of the sheath;
   an illuminating element disposed within the lumen adjacent to the image sensor;
   a working channel disposed within the lumen, the working channel comprising a distensible portion that extends past at least a portion of the image sensor; and
   a piezoelectric element sized to fit within the working channel, the piezoelectric element comprises a transducer coupled to a working tip with an intervening wire, the piezoelectric element configured to move the working tip via the wire when electricity is applied to the transducer, the working tip configured to puncture a tissue when the working tip is moved as a result of electricity being applied to the transducer
   wherein the transducer is disposed distal of the image sensor when the working tip extends distally beyond the opening at the distal-most end of the sheath.

2. The endoscopy system of claim 1, wherein the tissue comprises bone.

3. The endoscopy system of claim 1, wherein the working tip has a hardness of at least 6.5 on Mohr's scale.

4. The endoscopy system of claim 1, wherein the working tip comprises a material selected from the group consisting of steel, tungsten, titanium, a shape memory material, and plastic.

5. The endoscopy system of claim 4, wherein the shape memory material is nitinol.

6. The endoscopy system of claim 1, wherein the working tip is adapted to perform a microfracture procedure on the tissue, the tissue comprising a bone of a human patient.

7. The endoscopy system of claim 1, further configured for performing a procedure on a connective tissue, the system comprising:
a hooked blade sized to fit within the working channel, the hooked blade comprising a convex distal-facing surface and a concave proximal-facing cutting surface, the convex distal-facing surface having a smoothness sufficient to atraumatically distend the distensible portion of the working channel as the hooked blade is advanced distally past the image sensor.

8. The endoscopy system of claim 7, wherein the connective tissue comprises a carpal ligament.

9. The endoscopy system of claim 7, wherein the blade comprises a material selected from the group consisting of steel, tungsten, titanium, a shape memory material, and plastic.

10. The endoscopy system of claim 9, wherein the shape memory material is nitinol.

11. The endoscopy system of claim 7, wherein the concave proximal-facing cutting surface has a sharpness sufficient to incise the connective tissue.

12. The endoscopy system of claim 7, wherein the working channel proximal to the image sensor is configured to accommodate the hooked blade before the hooked blade is advanced distally past the opening.

13. The endoscopy system of claim 7, wherein the hooked blade deforms to a low-profile configuration when confined within the working channel.

14. The endoscopy system of claim 1, further comprising:
a stylet configured to perform an arthroscopic procedure with the sheath;
the stylet sized to fit within the working channel, and
the stylet having a rigidity sufficient to bend the distal portion of the sheath when the stylet is advanced distally past at least a portion of the image sensor.

15. The endoscopy system of claim 1, wherein the working channel is also sized to accommodate a hooked blade for a procedure on a connective tissue or a stylet for an arthroscopic procedure.

16. An endoscopy system comprising:
a sheath comprising a lumen and an opening at a distal-most end of the sheath, a distal portion of the sheath being deformable;
an image sensor disposed within the lumen of the distal portion of the sheath;
an illuminating element disposed within the lumen adjacent to the image sensor;
a working channel disposed within the lumen, the working channel comprising a distensible portion that extends past at least a portion of the image sensor; and
a piezoelectric element sized to fit within the working channel, the piezoelectric element comprises a transducer coupled to a working tip with an intervening wire, the piezoelectric element configured to move the working tip via the wire when electricity is applied to the transducer, the working tip configured to puncture a tissue when the working tip is moved as a result of electricity being applied to the transducer;
wherein the transducer is disposed proximal of the image sensor when the working tip extends distally beyond the opening at the distal-most end of the sheath.

* * * * *